United States Patent
Sveningsson

(10) Patent No.: US 9,981,055 B2
(45) Date of Patent: May 29, 2018

(54) CAP STERILIZATION

(71) Applicant: TETRA LAVAL HOLDINGS & FINANCE S.A., Pully (CH)

(72) Inventor: Philip Sveningsson, Bredaryd (SE)

(73) Assignee: TETRA LAVAL HOLDINGS & FINANCE S.A., Pully (CH)

( * ) Notice: Subject to any disclaimer, the term of this patent is extended or adjusted under 35 U.S.C. 154(b) by 0 days. days.

(21) Appl. No.: 15/118,765

(22) PCT Filed: Feb. 11, 2015

(86) PCT No.: PCT/EP2015/052884
§ 371 (c)(1),
(2) Date: Aug. 12, 2016

(87) PCT Pub. No.: WO2015/121308
PCT Pub. Date: Aug. 20, 2015

(65) Prior Publication Data
US 2017/0056541 A1     Mar. 2, 2017

(30) Foreign Application Priority Data

Feb. 13, 2014 (SE) ..................... 1450162

(51) Int. Cl.
*A61L 2/00* (2006.01)
*A61L 9/00* (2006.01)
(Continued)

(52) U.S. Cl.
CPC .............. *A61L 2/208* (2013.01); *A61L 2/22* (2013.01); *A61L 2202/122* (2013.01); *A61L 2202/23* (2013.01)

(58) Field of Classification Search
CPC .......... B65B 55/01; B67B 3/003; A61L 2/208; A61L 2/18; A61L 2/186
(Continued)

(56) References Cited

U.S. PATENT DOCUMENTS

2011/0142731 A1    6/2011  Beckmann et al.
2011/0150699 A1    6/2011  Ceci et al.
(Continued)

FOREIGN PATENT DOCUMENTS

EP     2 687 478 A1    1/2014
EP     2 740 495 A1    6/2014

OTHER PUBLICATIONS

International Search Report (PCT/ISA/210) dated Mar. 10, 2015, by the European Patent Office as the International Searching Authority for International Application No. PCT/EP2015/052884.
(Continued)

*Primary Examiner* — Monzer R Chorbaji
(74) *Attorney, Agent, or Firm* — Buchanan Ingersoll & Rooney PC

(57) ABSTRACT

The invention relates to a device for sterilization of the interior surface of packaging containers with electron beam, comprising an emitter provided with an electron exit window. The emitter is adapted to emit charge carriers, such as electrons, through the electron exit window, said electrons forming an electron cloud. The device comprises at least one outlet adapted to provide a flow of sterile gaseous medium adapted to maintain a local aseptic zone around at least an emitter portion including the electron exit window, thus preventing any flow of medium from outside the local aseptic zone from coming into the local aseptic zone. The invention also relates to a method.

14 Claims, 1 Drawing Sheet

(51) Int. Cl.
*A61L 2/20* (2006.01)
*A61L 2/22* (2006.01)

(58) Field of Classification Search
USPC ............... 422/1, 28, 32, 292, 298, 300, 305
See application file for complete search history.

(56) References Cited

U.S. PATENT DOCUMENTS

| | | |
|---|---|---|
| 2011/0158846 A1 | 6/2011 | Boschi et al. |
| 2011/0311399 A1* | 12/2011 | Silvestri .................. A61L 2/22 422/110 |
| 2013/0004368 A1 | 1/2013 | Morita et al. |
| 2013/0243648 A1 | 9/2013 | Buchhauser et al. |

OTHER PUBLICATIONS

Written Opinion (PCT/ISA/237) dated Mar. 10, 2015, by the European Patent Office as the International Searching Authority for International Application No. PCT/EP2015/052884.

Swedish Office Action dated Aug. 28, 2014 for Swedish Application No. 1450162-1 (5 pages).

* cited by examiner

CAP STERILIZATION

TECHNICAL FIELD

The present disclosure concerns a cap chamber for sterilizing caps or closures, and a method for sterilizing caps.

TECHNICAL BACKGROUND

In filling of commercially sterile products into sterilized packaging containers it is important that all components of the packaging container are sterilized. With "all components" we refer to all components having a surface to which the contents of the packaging container may have access, and as minimum requirement at least that particular surface should be sterilized. In a wider perspective it may be desired to sterilize such components fully, or at least to sterilize a greater area than what is included in the surface that will be in contact with the contents of the packaging container. One reason may be to prevent the occurrence of reinfection, i.e. the migration of contaminants from a non-sterile to a sterile area, another may be to prevent contaminants from entering an otherwise sterile area.

In the present disclosure the word "sterile" is frequently used. For most applications the definition conforms to the definition of "commercially sterile". For all applications it will conform to the definition "sterile enough for the purposes of the application" and "sterilization" and similar may be defined as "treatment with a sterilant until sterile".

SUMMARY

To this end the present invention relates to a device and a method for sterilizing caps. As used herein caps are meant to include several types of closure arrangements, such as screw caps, flip caps, snap caps, sports caps, and closure arrangements comprising a cap and a portion of a packaging container, which will be described in greater detail in the description referring to the drawings.

According to one aspect the present disclosure relates to a cap sterilization device comprising a sterilization chamber having a cap inlet and a cap outlet and guide means for guiding caps through the sterilization chamber. The device further comprises a nozzle for injecting a sterilant into the sterilization chamber and at least two exhaust outlets for evacuation of gases from the sterilization chamber.

According to one or more embodiments the nozzle may be arranged to inject gaseous sterilant towards an open end of the caps.

In one or several embodiments the first exhaust outlet may be arranged in the cap inlet and a second exhaust outlet may be arranged in the cap outlet.

The caps may be arranged to be indexed forward in an intermittent manner while the nozzle is arranged to provide a continuous flow of sterilant.

A valve may be arranged upstream the nozzle, between the nozzle and a vaporizer, the nozzle being able to selectively redirect a flow from the vaporizer into an exhaust manifold instead of to the nozzle.

The nozzle may be arranged to provide an amount of sterilant such that the concentration in the sterilization chamber varies with less than 25% over a volume defined by the first exhaust outlet and the second exhaust outlet, counted as maximum concentration compared to minimum concentration in the volume.

In any embodiment the sterilant may comprise hydrogen peroxide, or a mixture of components one of which is hydrogen peroxide. Other examples may include peracetic acid (PAA) and compounds thereof, or other sterilization agents or sterilants.

According to a second aspect the intention relates to a method for sterilizing caps.

DETAILED DESCRIPTION

Figure 1:
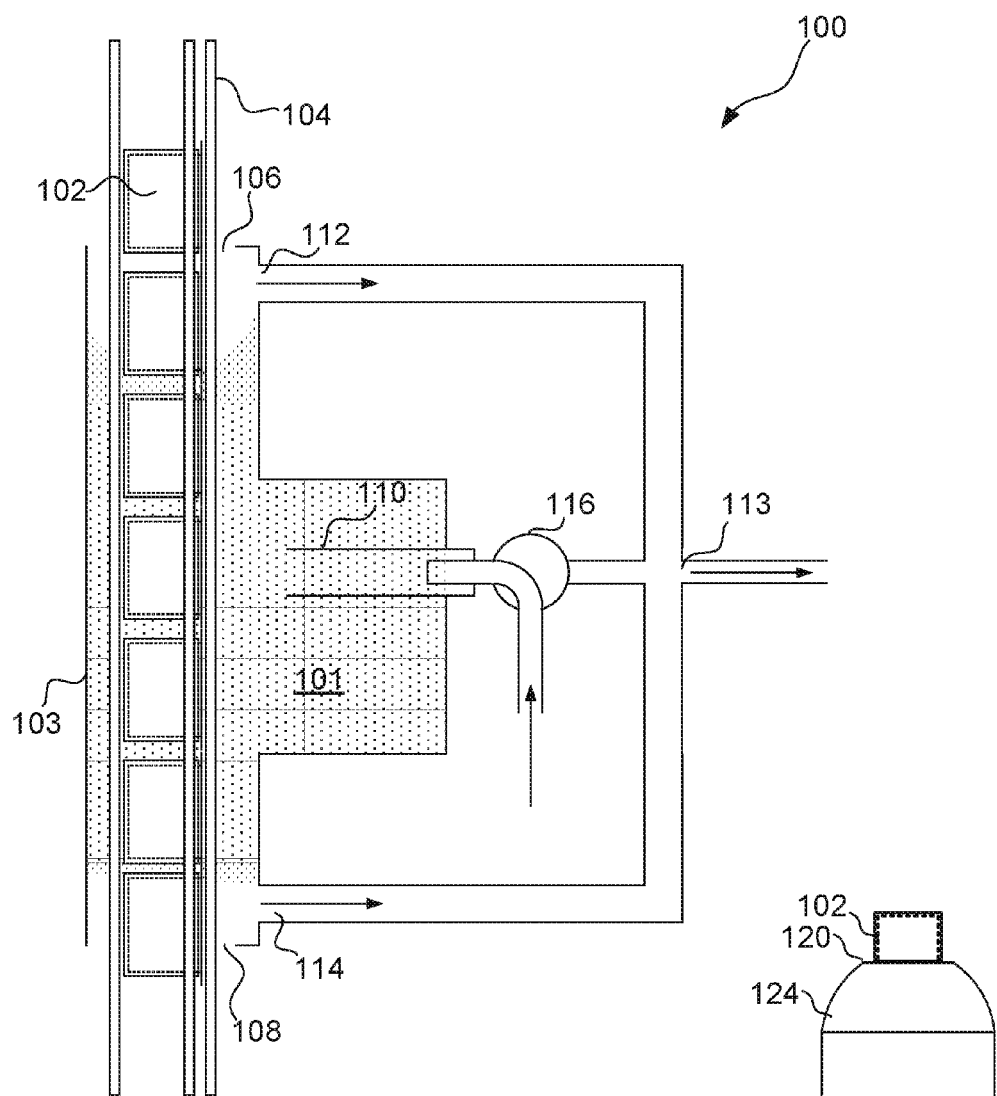
FIG. 1 shows a cross sectional side view of a sterilization device, or at least a schematic illustration thereof.

FIG. 1 is a schematic cross section of a sterilization device 100 having a sterilization chamber 101. The sterilization device 100 is shown from one side thereof. Caps 102 are arranged to follow guide means 104 through the sterilization chamber 101. The caps 102 enter via a cap inlet 106 and exits via a cap outlet 108. In the present embodiment the caps 102 are fed by gravity, and once a cap 102 is removed from the guide means 104 downstream the sterilization chamber 101 the entire line of caps 102 is incremented one step downstream. The removal of caps 102 downstream may be performed in a step to move the cap 102 from the line of caps to a cap-application device or another processing step. The caps may in other instances be directed to storage, awaiting later use. The one-by-one removal of caps will generate the intermittent motion pattern of caps. The sterilization device 100 as disclosed herein may in other embodiments be based on a continuous motion pattern. Furthermore, it is foreseeable to arrange another type of drive, yet use of gravity vouches for simplicity and a non-complex construction inside the sterilization chamber 101.

Inside the sterilization chamber 101 there is a hydrogen peroxide nozzle 110 arranged to inject hydrogen peroxide into the chamber 101. The nozzle 110 is furthermore arranged to inject the hydrogen peroxide towards the caps 102. In particular the nozzle 110 may be arranged to inject a spray towards and impact an area surrounding a particular cap position such as to fully reach all portions of a cap. It is preferable that the sterilant is injected in gaseous form. For this reason there is a vaporization device arranged upstream the nozzle 110. As a non-limiting example the temperature in the vaporization device may be 210° C. and for one particular embodiment the consumption includes 0.7 l/h of hydrogen peroxide (3% concentration by volume) and the addition of about 80 l/min of air. All of these parameters may shift depending on the preferred level of sterilization and of the size of the sterilization chamber etc.

Exhausts 112, 114 are arranged at the cap outlet 108 and the cap inlet 106 respectively. The exhausts ensure that the amount of hydrogen peroxide released to the atmosphere is kept at an absolute minimum, or is completely avoided, by evacuating it to a exhaust manifold leading to a destruction device (not shown). Rather than necessarily having an underpressure, i.e. a lower pressure inside the sterilization chamber than in the immediate surroundings, to prevent hydrogen peroxide or any other sterilant from leaving the sterilization chamber, the present sterilization chamber 101 rather controls gas flows locally in the area of the inlet 106 and the outlet 108 respectively. Thus the exhausts 112, 114 efficiently prevents gas passage into and out from the sterilization chamber 101. Furthermore, the sterilant containing atmosphere of the sterilization chamber 101 will be pulled towards both the inlet 106 and towards the outlet 108, meaning that as soon as a cap 102 enters through the inlet 106 the sterilization treatment will commence. When passing an impact area of the sterilization spray the cap 102 will experience a maximum load of sterilant, after which the concentration may gradually decrease, yet be maintained, until the cap 102 leaves the sterilization chamber 101 through the outlet 108. It may be emphasized that the caps 102 pass the sterilization chamber 101 with their open end directed towards the hydrogen peroxide nozzle 110. An effect of the present setup is that there will be a generally elevated concentration of sterilant in the sterilization chamber such that surfaces not reached directly by the sterilant spray provided by the nozzle 110 will still be exposed to such high concentrations of sterilant that adequate sterilization is enabled. Consequently the purpose of the nozzle 110 is not merely to supply an adequate amount of sterilant to the interior of a cap 102, but also to ensure an adequate concentration of sterilant in the sterilization chamber as a whole. In the present embodiment the nozzle 110 is arranged in such a way that it is aligned with a particular cap position, meaning that as the caps are moved incrementally through the sterilization chamber they will all at one position be facing the sterilization nozzle 110, and the spray will be directed to the interior of the cap 102.

After application and as the surface temperature of the cap 102 increases the condensed sterilant will start to vaporize such that a minimum amount of sterilant leaves the sterilization chamber via the caps. Furthermore, the flow balance of the sterilization chamber will be such that there is a flow of surrounding air entering through the outlet and the inlet respectively, and even though this air will leave through the nearest exhaust it will still fulfil a function of preventing sterilant from leaving into the surroundings. The source of heat is in the present embodiment only the heated sterilant spray, and the caps are only tempered by means of being stored in a particular temperature before being fed to the cap sterilization device. The present case does not exclude the possibility of using heaters (or coolers) to temper the caps or the sterilization device, if needed to increase controllability.

As a further effect the concentration of sterilant will be evenly distributed within the constraints of the sterilization chamber 101, at least in a volume defined by the first exhaust outlet 112 and the second exhaust outlet 114 as indicated by the dotted area in FIG. 1. The boundaries of the dotted area should not be construed as exact. In particular, the flow around the cap in the vicinity of the exhaust outlets may vary a bit, but given that the variation in the concentration of sterilant within the defined area may be less than 25%, the main variations being formed in the boundaries. Outside of the boundaries the concentration of sterilant may be negligent since surrounding air free from sterilant may be pulled in to the cap inlet and the cap outlet and straight into the exhaust outlets 112 and 114 respectively. To that end the present device provides sterilization by means of a direct spray of sterilant combined with an overall increased concentration of sterilant providing a topical sterilization of all accessible surface of a cap 102 sterilized in the sterilization chamber 101.

It is preferred that the sterilant leaves the nozzle 110 in a continuous manner in order to maintain a desired concentration of sterilant inside the sterilization chamber 101. In the event of unexpected stops downstream the sterilization chamber a valve 116 may be switched directing the flow of sterilant directly to an exhaust manifold 113 rather than into the sterilization chamber through the nozzle 110. In such a case the signal to the valve to effect the switch will come from a control unit the details of which are not relevant for explaining the present device.

The guide means 104 are arranged to localize the caps 102 during their passage through the sterilization chamber. While fulfilling that main purpose they should avoid shadowing (covering) too much of the caps 102, since that may inhibit proper sterilization. Also, the guide means 104 are arranged to maintain a distance between the caps 102 and a back wall of the sterilization chamber 101, i.e. the wall remote to the hydrogen peroxide nozzle 110. The purpose is to enable hydrogen peroxide to reach all surfaces of each cap. To that end it may be preferred to introduce the caps through the inlet 106 at a temperature being below the condensation point of the sterilant at prevailing conditions. In this way the sterilant will condensate at all surfaces of the cap or closure 102. In the present embodiment the guide means comprises a number of rails 104 with a circular cross section, yet other options should be readily available for the skilled person.

Figure 2:
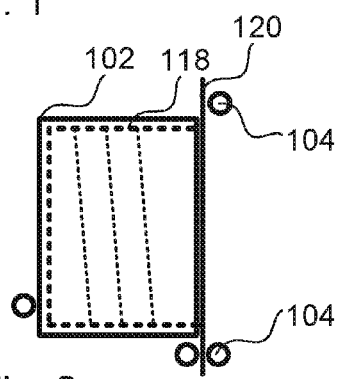
FIG. 2 is a detailed view, still schematic, of a cap.

FIG. 2 is a view in the a longitudinal axis of the guide means 104, i.e. a partial view from above of FIG. 1, illustrating one example of how guide means may be arranged. In the particular setup shown the caps 102 may be caused to rotate along a longitudinal axis (an axis extending parallel to an axis of rotational symmetry of the cap. As shown in FIG. 2 there are more guiderails 104 arrange to one side of the cap 102. This may generate a frictional force breaking this side in relation to the other side, which may cause a rotational motion as the cap travels through the sterilization chamber 101. Due to the rotation more surfaces of the cap will be fully exposed to the hydrogen peroxide spray. There are obviously a number of ways of accomplishing rotation of the caps as they travel through the sterilization chamber 101. The general approach of creating more friction on one side than on the other is a simplistic and efficient method, yet other method e.g. based on an individual drive for the rotation would in principle also be possible.

Figure 3:
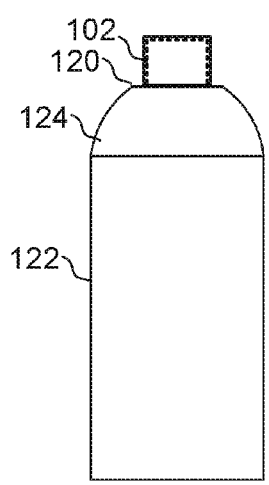
FIG. 3 a schematic side view of a packaging container.

While viewing the more detailed view of FIG. 2 it may be worth mentioning that while the word cap is used in the present description and while the item being sterilized may actually be a cap according to any definition, a closure arrangement may be more suitable in the context of the embodiment shown in FIG. 2, as was mentioned in the summary portion. For the sake of simplicity "cap" is used to designate all such closure arrangements. For the sake of explaining the closure arrangement shown in FIG. 2, it the cap 102 and a portion of the neck, including a threaded neck 118 and an attachment flange 120. Such attachment flange may be utilized when arranging the closure arrangement onto a packaging container. The packaging container 122, as shown in FIG. 3, may comprise a packaging-laminate sleeve 124 e.g. made from a packaging laminate comprising plastic and paper layers as is commonly used. The sleeve 124 may be directly fused to the closure arrangement, yet the two components may also be connected via a plastic shoulder portion 126. An example of such a packaging container is the one commercialized under the name Tetra Evero® Aseptic. In still other embodiments the 120 may be used to attach the closure arrangement onto a flat or folded piece of packaging laminate. Examples of this latter packaging container may be the ones commercialised by the present applicant under the names, Tetra Rex®, Tetra Gemina® Aseptic, Tetra Brik® Aseptic, etc.

The invention claimed is:

1. A cap sterilization device comprising a sterilization chamber having a cap inlet and a cap outlet and guide means for guiding caps through the sterilization chamber, the device further comprising a nozzle for injecting a sterilant into the sterilization chamber and at least two exhaust outlets for evacuation of gases from the sterilization chamber, wherein a first exhaust outlet is arranged in the cap inlet and a second exhaust outlet is arranged in the cap outlet, wherein
a valve is arranged upstream from the nozzle, between the nozzle and a vaporizer, the valve being configured to selectively redirect a flow from the vaporizer into an exhaust manifold instead of to the nozzle, based on input from a control system.

2. The cap sterilization device of claim 1, wherein the nozzle is arranged to inject gaseous sterilant towards an open end of the caps.

3. The cap sterilization device of claim 1, wherein the caps are arranged to be indexed forward in an intermittent manner while the nozzle is arranged to provide a continuous flow of sterilant.

4. The cap sterilization device of claim 1, wherein the first exhaust outlet and the second exhaust outlet define a boundary outside of which the concentration of the sterilant is negligible, wherein the first exhaust outlet and the second exhaust outlet are arranged to pull gas free from sterilant outside of the boundary into the cap inlet and the cap outlet and further into the first exhaust outlet and the second exhaust outlet.

5. The cap sterilization device according to claim 1, wherein the nozzle is arranged to provide an amount of sterilant such that the concentration in the sterilization chamber varies with less than 25% over a volume the borders of which are defined by the sterilization chamber, the first exhaust outlet and the second exhaust outlet.

6. The cap sterilization device according to claim 1, wherein the sterilant is hydrogen peroxide.

7. The cap sterilization device of claim 1, wherein the sterilization device is configured to induce rotation to the caps as they travel through the sterilization chamber.

8. A method for sterilization of caps by using a cap sterilization device according to claim 1, comprising intermittently feeding caps through a sterilization chamber and continuously subjecting them to sterilant injected via a nozzle, further comprising evacuating gas from the sterilization chamber via two exhaust outlets located in the cap inlet and the cap outlet of the sterilization chamber respectively.

9. The cap sterilization device according to claim 1, wherein
the guide means extend beyond the sterilization chamber in the conveying direction, and
the first exhaust outlet and the second exhaust outlet are positioned to communicate with both sterilized gas possessing the sterilant and external gas devoid of the sterilant such that the sterilized gas and the external gas are drawn into the cap inlet and the cap outlet and further into the first exhaust outlet and the second exhaust outlet.

10. The cap sterilization device according to claim 1, wherein gravity moves the caps along the guide means in the conveying direction.

11. The cap sterilization device according to claim 1, wherein the cap sterilization device possesses a width perpendicular to the conveying direction of the caps, the width of the cap sterilization device at the sterilization chamber being greater than the width of the cap sterilization device at the cap inlet and at the cap outlet.

12. A cap sterilization device that sterilizes caps which are later applied to form part of respective packaging containers, the cap sterilization device comprising:
a guide configured to receive a plurality of the caps which each include an open end, the guide comprising plural rails spaced apart from one another;
a sterilization chamber through which the guide passes to convey the caps through the sterilization chamber in a conveying direction;
the sterilization chamber including a cap inlet through which the caps pass when entering the sterilization chamber while being conveyed by the guide, a cap outlet through which the caps pass when exiting the sterilization chamber while being conveyed by the guide, the cap outlet being positioned downstream of the cap inlet with reference to the conveying direction;
a nozzle positioned in the sterilization chamber and facing toward the guide to inject sterilant into the sterilization chamber and toward the open end of each cap as the cap passes in front of the nozzle, the nozzle being located between the cap inlet and the cap outlet considered with reference to the conveying direction;
a first exhaust outlet positioned in the cap inlet to evacuate gas from the sterilization chamber;
a second exhaust outlet positioned in the cap outlet to evacuate gas from the sterilization chamber; and
a valve is arranged upstream from the nozzle, between the nozzle and a vaporizer, the valve being configured to selectively redirect a flow from the vaporizer into an exhaust manifold instead of to the nozzle, based on input from a control system.

13. The cap sterilization device according to claim 12, wherein the cap sterilization device possesses a width perpendicular to the conveying direction of the caps, the width of the cap sterilization device at the sterilization chamber being greater than the width of the cap sterilization device at the cap inlet and at the cap outlet.

14. The cap sterilization device according to claim 12, wherein the plural rails spaced apart from one another include a greater number of rails on one side of the caps when the caps are being conveyed than on an other side of the caps opposite to the one side when the caps are being conveyed, such that the rails cause a rotation motion of the caps when the caps are being conveyed by the guide.

* * * * *